United States Patent [19]

Sugimoto et al.

[11] Patent Number: 5,114,261

[45] Date of Patent: May 19, 1992

[54] SWASHPLATE TYPE HYDRAULIC DEVICE HAVING A BALL JOINT CONNECTION

[75] Inventors: Kimiyasu Sugimoto; Hajime Yoshino, both of Saitama, Japan

[73] Assignee: Honda Giken Kogyo Kabushiki Kaisha, Tokyo, Japan

[21] Appl. No.: 559,037

[22] Filed: Jul. 30, 1990

[30] Foreign Application Priority Data

Jul. 31, 1989 [JP] Japan .................. 1-198557
Aug. 7, 1989 [JP] Japan .................. 1-204288
Feb. 19, 1990 [JP] Japan .................. 2-38036

[51] Int. Cl.⁵ ............... F16C 11/06; F04B 27/08
[52] U.S. Cl. .................. 403/122; 403/353; 417/269; 92/187
[58] Field of Search .......... 403/122, 124, 126, 128, 403/115, 114, 348, 353, 165, 56, 76; 92/71, 187; 417/269, 222 S, 222 R; 74/60

[56] References Cited

U.S. PATENT DOCUMENTS

| | | | |
|---|---|---|---|
| 3,192,868 | 7/1965 | Wahlmark | 403/122 X |
| 3,589,756 | 6/1971 | Pruvot | 403/124 |
| 3,787,128 | 1/1974 | Maistrelli | 403/122 X |
| 3,795,922 | 3/1974 | Herbert et al. | 403/76 X |
| 3,871,782 | 3/1975 | Johansson et al. | 403/122 |
| 4,225,260 | 9/1980 | Gaines | 403/114 |
| 4,279,041 | 7/1981 | Buchholz | 403/353 X |
| 4,815,327 | 3/1989 | Drevet | 417/269 X |
| 4,860,641 | 8/1989 | Spears | 417/269 X |

FOREIGN PATENT DOCUMENTS

| | | | |
|---|---|---|---|
| 2307641 | 2/1973 | Fed. Rep. of Germany | 403/122 |
| 2018916 | 4/1976 | Fed. Rep. of Germany | |
| 62-218664 | 9/1987 | Japan | |
| 475455 | 11/1937 | United Kingdom | |
| 840015 | 7/1960 | United Kingdom | |

*Primary Examiner*—Peter M. Cuomo
*Attorney, Agent, or Firm*—Armstrong & Kubovcik

[57] ABSTRACT

A swashplate type hydraulic device has a ball joint which includes a spherical socket of a major arc longitudinal section formed in a plunger or a shoe member and a ball formed at an end of a connecting rod which connects the plunger and the shoe member, the ball being fitted in the socket so as to permit a swing motion of the rod around the ball, the inlet of the socket having a center offset by a predetermined amount of distance from the center of the socket while the ball having a cylindrical portion which can be fitted in the inlet and which has a center located offset from the center of the ball by an amount equal to the offset amount of the inlet center relative to the socket center, the centers of the inlet and the cylindrical portion being offset relative to each other in a fitted state of the socket and ball. The ball includes a chamferred portion to permit the ball to be fitted in the socket when the rod is at a position outside its normal swinging range. The ball and socket can have an increased strength against disassembly even when they are subjected to surface hardening before assembly.

8 Claims, 10 Drawing Sheets

SWASHPLATE TYPE HYDRAULIC DEVICE HAVING A BALL JOINT CONNECTION

BACKGROUND OF THE INVENTION

1. Field of the Invention

The field of the invention is swashplate type hydraulic devices applicable to hydraulic pump and motor and more particularly is such devices as comprising a cylinder block, a plurality of plungers arranged annularly around the axis of the block and slidably fitted therein, a shoe member disposed at an angle to the block axis for synchronous rotation with the block, and connecting rods each of which is connected at opposite ends to the shoe member and associated plunger via ball joints, at least one of the joints comprising a spherical socket of a major arc longitudinal section formed in the plunger or shoe member, and a ball formed at one end of the rod and fitted in the socket for swing motion of the rod around the ball.

2. Description of the Prior Art

As conventional hydraulic devices of the mentioned type there are known one in which the ball is formed with an annular chamferred portion which is coaxial with the rod and has a diameter slightly larger than the socket inlet and the ball is fitted in the socket by pressfitting the chamferred portion to the socket inlet (see Japanese Patent Publication Kokai No. 62-218664, for example), and one wherein the socket inlet is previously formed of a diameter substantially equal to that of the ball and after inserting the ball into the socket, the inlet is caulked so as to have a reduced diameter (see Japanese Patent Publication Kokoku No. 55-14272).

In the former case, the socket and ball can be subjected to surface hardening treatment such as by GNS or Sulphurizing prior to their fitting. However, their disassembly is prevented only by the press-fitting of the ball into the socket inlet, so that the strength against disassembly is relatively low. On the other hand, in the latter case, the socket and ball cannot be subjected to surface hardening treatment prior to their fitting operation and hence a joint structure obtained thereby will be inferior in anti-friction property.

SUMMARY OF THE INVENTION

The present invention has been proposed in view of such circumstances and an object thereof is to provide a hydraulic device which includes a ball joint of the mentioned type but having a high strength against disassembly and capable of being subjected to surface hardening prior to fitting of the components.

In order to achieve the object, according to the first feature of the invention, there is provided a swashplate type hydraulic device wherein the socket has an inlet whose center is offset by a predetermined amount of distance from the center of the socket so as to inscribe at a periphery of the inlet the profile of the socket when viewed in a plan from the side of the inlet, and the ball is formed with a cylindrical portion which has a center offset from the center of the ball by an amount equal to and which is capable of fitting into the inlet, the centers of the inlet and the cylindrical portion being offset relative to each other in a state of the ball being fitted into the socket.

The above arrangement enables the socket and ball to be subjected to surface hardening treatment before their fitting.

In addition, if the socket and ball are rotated relative to each other at angle of about 180° around their centers, then the centers of the inlet and the cylindrical portion become deviated largely from each other and hence the ball is reliably prevented from falling off the socket at any swung position of the connecting rod.

According to the second feature of the invention, there is provided a swashplate type hydraulic device wherein the ball is formed with an annular chamferred portion for permitting fitting of the ball into the socket when the connecting rod assumes a position relative to the socket outside an angle of normal swinging motion of the rod.

This arrangement also enables a surface hardening treatment for the socket and ball before fitting operation.

Furthermore, since the axis of the chamferred portion does not come into alignment with the center of the socket inlet within the normal range of swing motion of the connecting rod, the ball joint can be assured a high strength against disassembly during operation of the hydraulic device and the joint may not be disassembled even upon receiving a tensile load thereon.

According to the third feature of the invention, there is provided a swashplate type hydraulic device wherein the connecting rod is formed with a hydraulic fluid port which extends along the axis of the rod to provide a communication between the cylinder block and the shoe member, and the socket has an inlet whose center is offset by a predetermined amount of distance from the center of the socket, the ball being formed with a tubular chamferred portion for permitting fitting of the ball into the socket inlet when the connecting rod is inclined by a predetermined angle in a predetermined direction to a position outside the range of normal swing motion of the rod, the chamferred portion having a center offset relative to the center of the ball by an amount equal to the offset amount of the center of the inlet relative to the socket center and in a direction opposite to the inclined direction of the connecting rod.

This arrangement permits the distances from respective points on the chamferred portion to the port opening at an end of the ball along the ball surface to be uniformalized when the connecting rod is utilized to provide a fluid passage between the cylinder block and the shoe member, and further serves to suppress fluid leakage from the port opening to the chamferred portion to a possible extent.

The above and other objects, features and advantages of the present invention will become apparent from reading the following detailed description of preferred embodiments taken in conjunction with the accompanying drawings.

BRIEF DESCRIPTION OF THE DRAWINGS

FIGS. 1-5 show a first embodiment according to the present invention, wherein FIG. 1 is a longitudinally sectional view of an essential portion of a swashplate type hydraulic pump according to this embodiment, FIG. 2 is a view of a ball joint in a disassembled state.

FIGS. 6-9 show a second embodiment according to the invention, wherein FIG. 6 is a longitudinally sectional view corresponding to FIG. 1, FIG. 7 is a longitudinally sectional view of a ball joint in a disassembled state. FIG. 8 is a longitudinally sectional view of the ball joint upon assembly, and FIG. 9 is a longitudinally sectional view of the ball joint in a state thereof when associated connecting rod performs a normal range of swinging motion;

FIGS. 10 and 11 show a third embodiment according to the invention, wherein FIG. 10 is a longitudinally sectional view corresponding to FIG. 8 and FIG. 11 is a sectional view taken along a line XI—XI of FIG. 10; and FIGS. 12-15 show a fourth embodiment according to the invention, wherein FIG. 12 is a longitudinally sectional view corresponding to FIG. 1, FIG. 13 is a view showing a disassembled state of a ball joint, FIG. 14 is a view explaining the assembly of the ball joint and FIG. 15 is an enlarged longitudinally sectional view of the ball joint in a state of normal operation.

DESCRIPTION OF PREFERRED EMBODIMENTS

Some embodiments according to the invention will be described hereunder with reference to the drawings.

FIGS. 1-5 show the first embodiment according to the invention.

Figure 1:
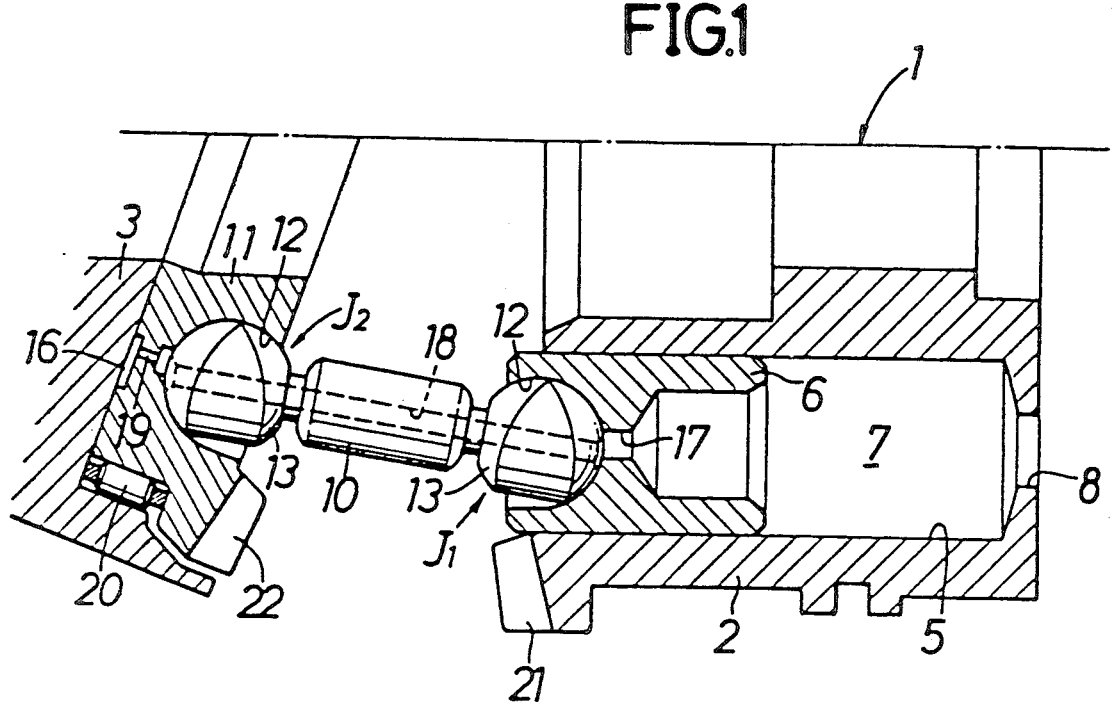

Referring first to FIG. 1, therein is shown a swashplate type hydraulic pump 1 as a swashplate type hydraulic device having a cylinder block 2 which is rotatably carried on a frame structure not shown. In FIG. 1, a swashplate 3 is disposed on the left side of the cylinder block 2 and a dispensing board, not shown, is on the right side of the block. The swashplate 3 is held inclined at a predetermined angle to the axis of the cylinder block 2.

The cylinder block 2 is formed therein with a plurality of cylinder bores 5 arranged at equal circumferential intervals around the axis of the block 2 so as to extend parallel to the block axis and open to the swashplate-side end surface of the block. A plunger 6 is slidably fitted into each cylinder bore 5.

A pump chamber 7 is defined between each plunger 6 and the closed end of associated cylinder bore 5 and a pump port 8 leading from the pump chamber 7 opens to an end surface of the cylinder block 2. This pump port 8 is controlled by the afore-mentioned dispensing board so as to be placed in communication with a low pressure part or a high pressure part of a hydraulic motor not shown.

The outer end of each plunger 6 is coupled with one of opposite ends of a connecting rod 10 via a ball joint $J_1$. The other end of the connecting rod 10 is in turn coupled via a ball joint $J_2$ to a unitary circular shoe member 11 which is carried rotatably on the inclined surface of the swashplate 3.

Figure 2:
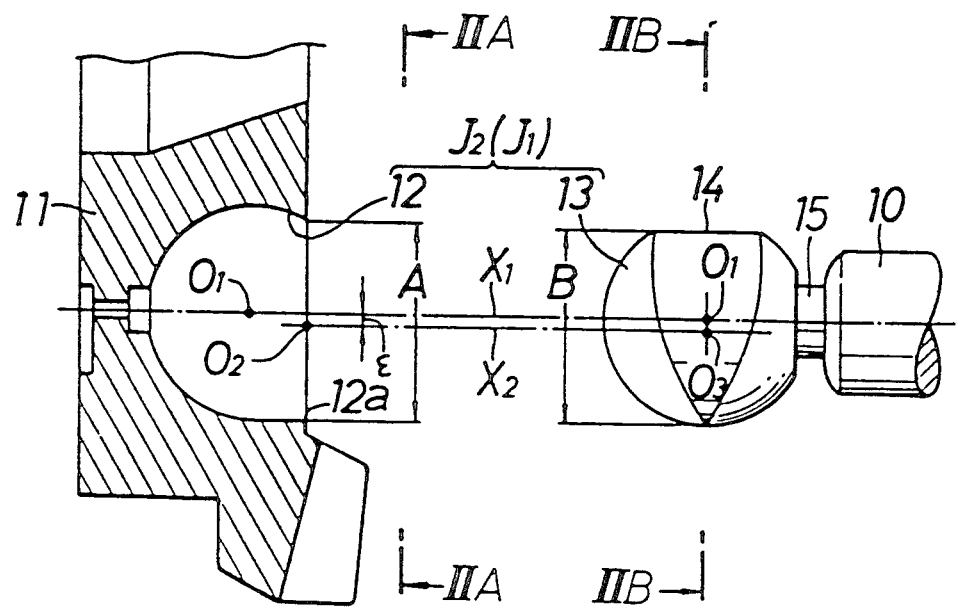
Figure 2A:
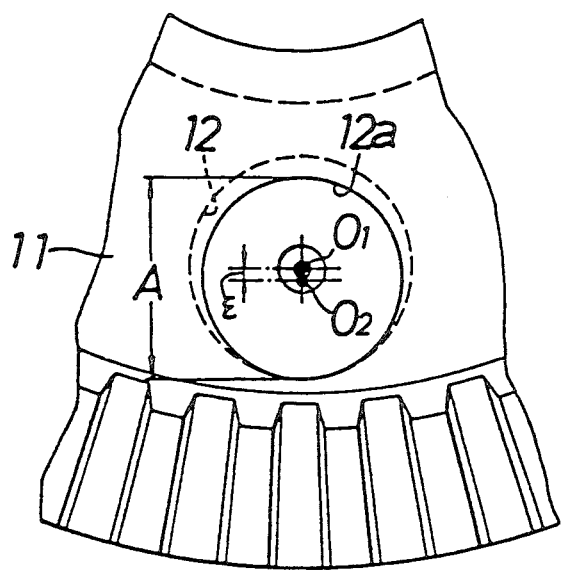
FIG. 2A is a view seen in the direction of an arrow IIA—IIA in FIG. 2.
Figure 2B:
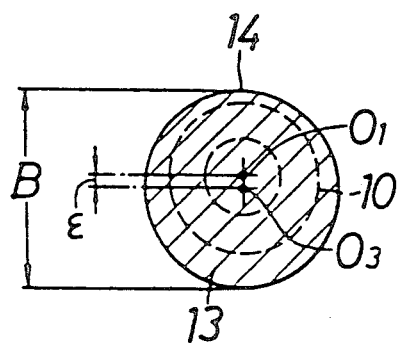
FIG. 2B is a sectional view taken along a line IIB—IIB of FIG. 2, and FIGS. 3-5 are explanatory views an assembly process of the ball joint.

As shown in FIGS. 1 and 2, each of the ball joints $J_1$ and $J_2$ comprises a spherical socket 12 having a longitudinal section of major arc formed in the shoe member 11 or plunger 6 and a ball 13 which is formed continuously with the connecting rod 10 via a neck portion 15 and is fitted in the socket 12 for swinging motion therearound. The socket 12 has an inlet 12a that opens to the end surface of the shoe member 11 or plunger 6. The inlet 12a is formed such that its center is offset by a predetermined amount of distance $\epsilon$ from the center $O_1$ of the socket 12 and its peripheral edge inscribes the profile of the socket 12 when viewed in a plan from the inlet 12a side (see FIG. 2A). Reference character $O_2$ denotes the center of the inlet 12a in the figures.

On the other hand, the ball 13 is formed with a cylindrical portion 14 which is capable of fitting into the inlet 12a. This cylindrical portion 14 is formed such that upon assembly the center $O_3$ of the portion 14 comes to a position offset from the center $O_1$ of the ball 13 by the same amount of distance as the afore-mentioned offset amount of distance $\epsilon$.

Diameter B of the cylindrical portion 14 is determined according to the following conditions of use:

1. For a heavy load use . . . The diameter B of the cylindrical portion 14 is set equal to or slightly larger than the diameter A of the inlet 12a of the socket 12.
2. For a light load use . . . The diameter B of the cylindrical portion 14 is set slightly smaller than the diameter A of the inlet 12a of the socket 12.

Figure 3:
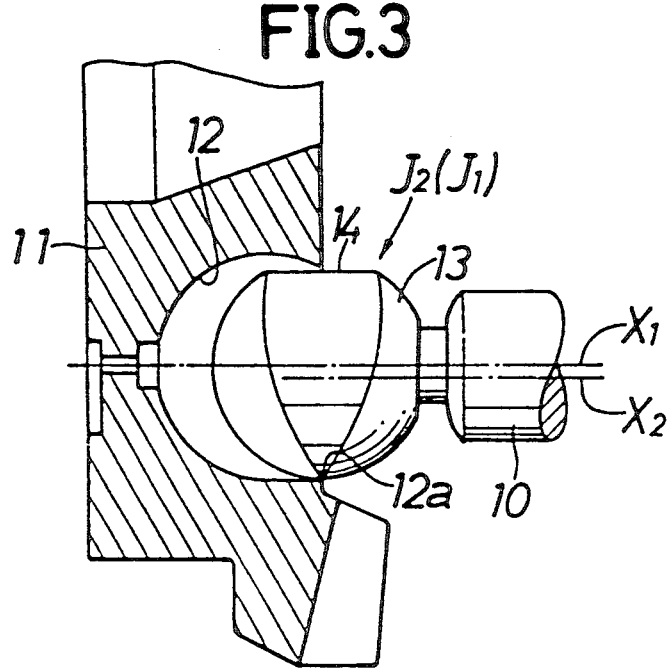
Figure 4:
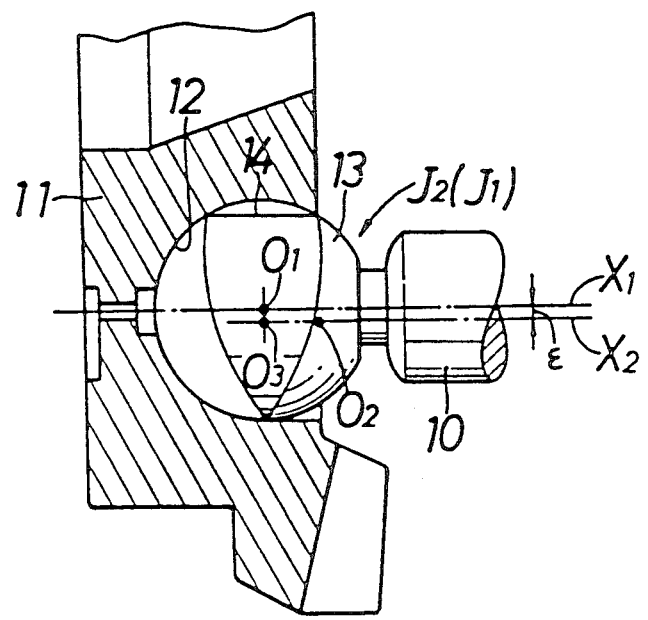

For assembly of the socket 12 and ball 13, after they have been subjected to surface hardening treatment, the inlet 12a of socket 12 and the cylindrical portion 14 of ball 13 are positioned on the same axis $X_2$ as shown in FIG. 2. In the above case 1, the cylindrical portion 14 is then press-fitted into the inlet 12a by means of a press-fitting machine as shown in FIG. 3 whereas in the case 2, the cylindrical portion 14 is manually inserted into the inlet 12a, whereby the ball 13 can be fitted into the socket 12 (see FIG. 4).

Figure 5:
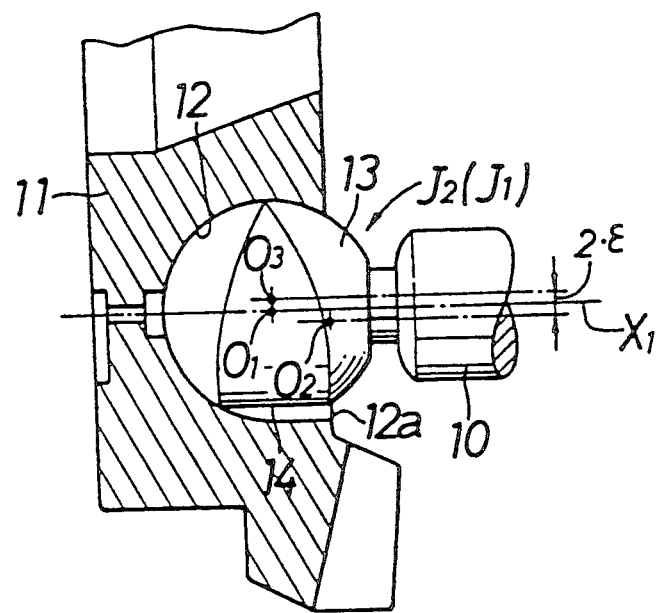
Figure 6:
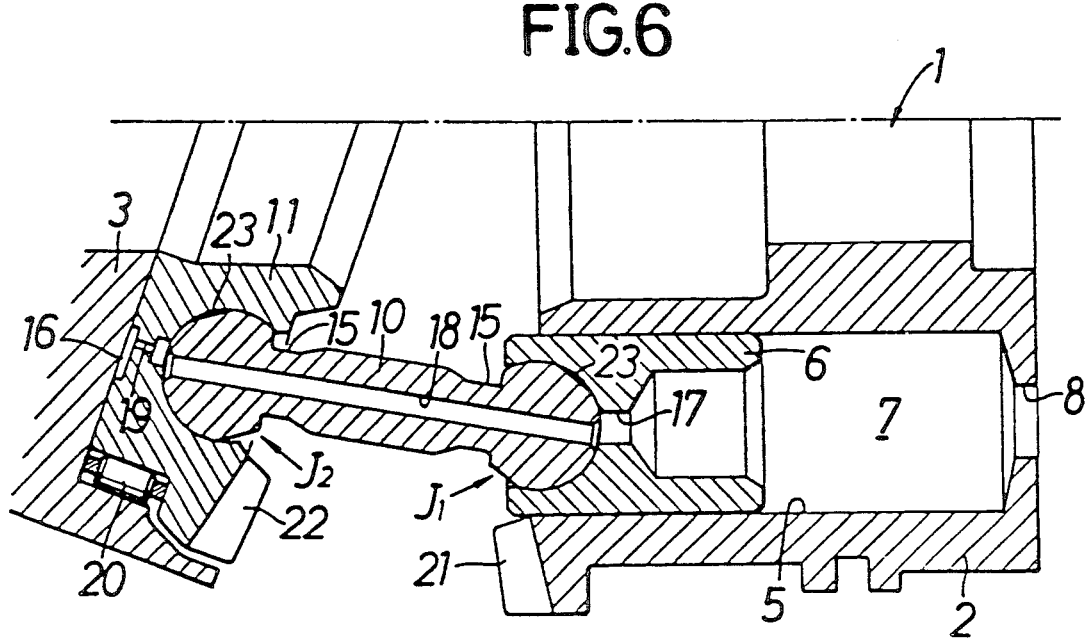
Figure 7:
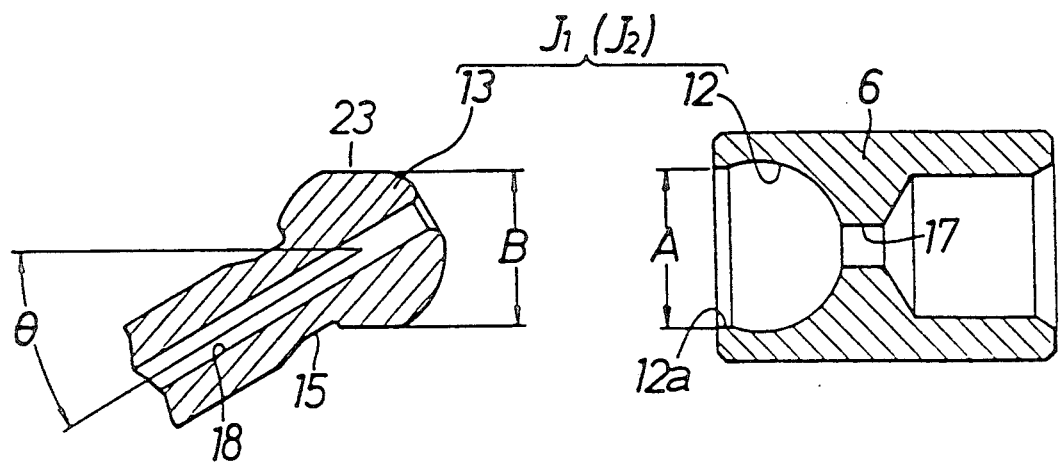

After the fitting operation, as shown in FIG. 5, the socket 12 and the ball 13 are rotated by an angle of about 180° relative to each other around the axis $X_1$ which passes the centers $O_1$ of the socket 12 and ball 13 and as a result thereof the centers of the socket inlet 12a and cylindrical portion 14 are largely deviated from each other by a distance of $2 \times \epsilon$. Accordingly, falling off of the ball 13 from the socket 12 can reliably be prevented.

On the sliding surface of the shoe member 11 opposed to the swashplate 3 there are provided a plurality of hydraulic pockets 16 in a manner corresponding to the sockets 12 and for connecting each the hydraulic pockets 16 with an associated pump chamber 7 a series of hydraulic fluid ports 17, 18 and 19 are provided through the plunger 6, connecting rod 10 and shoe member 11, respectively.

Bevel type synchronous gears 21 and 22 are formed on opposed surfaces of the cylinder block 2 and the shoe member 11 so as to be meshed with each other.

The operation of this embodiment will next be described.

When the cylinder block 2 is driven to rotate by a drive power source, not shown, the cylinder block 2 causes the shoe member 11 to rotate in synchronism therewith via the synchronous gears 21 and 22. In response to the rotation of the shoe member 11, plungers 6 which are located on a lower side of the inclined surface of the swashplate 3 are given a delivery stroke from the swashplate 3 via pressurize the associated pump chambers 7 whereas plungers 6 located on an upper side of the inclined surface of the swashplate 3 are given a suction stroke to decompress their associated pump chambers 7. In the suction stroke, the pump port 8 communicates with the low pressure part of the hydraulic motor via the dispensing board, not shown, and the working fluid in the low pressure part is sucked into the pump chamber 7. Meanwhile, the pump port 8 in the delivery stroke is placed in communication with the high pressure part of the hydraulic motor via the dispensing board and the working fluid which has been pressurized in the pump chamber 7 is fed to the high pressure part.

Moreover, since the pressurized fluid in the pump chamber 7 is partly fed to the hydraulic pocket 16 through the series of hydraulic fluid ports 17, 18 and 19 formed in the plunger 6, connecting rod 10 and shoe member 11, the hydraulic pressure can be used to support the thrust load acting on the shoe member 11 thus making the rotating movements of the shoe member 11 smooth.

Since the locus depicted by the center of the ball joint $J_2$ which connects the connecting rod 10 with the shoe member 11 is not included in one and the same cylindrical plane due to an inclined arrangement of the swashplate 3 during such an operation, the connecting rod 10 is caused to swing around the ball joint $J_1$ of the plunger 6 side as a fulcrum.

In this operation, at each of the ball joints $J_1$ and $J_2$, the socket 12 and the ball 13 will hardly be displaced relative to each other so as to bring the inlet 12a of socket 12 and the cylindrical portion 14 of ball 13 into alignment on the same axis $X_2$, so that the ball 13 can reliably be prevented from falling off the socket 12 at any swung position of the connecting rod 10.

FIGS. 6-9 show the second embodiment according to the invention and parts thereof corresponding to those of the first embodiment are designated by the same reference numerals and characters.

In this embodiment, it is specifically arranged that each ball 13 is formed with an annular chamferred portion 23 thereon and the generatrix for the chamferred portion 23 is determined so as to form an angle $\theta$ with respect to the axis of the connecting rod 10, which angle $\theta$ falls outside or is not included in an angle $\alpha$ defined by normal swinging movements of the connecting rod 10. A neck portion 15 of a small diameter is formed at a boundary area between the ball 13 and the rod portion of the connecting rod 10.

Diameter B of the chamferred portion 23 is determined according to the following conditions of use:

1. For a heavy load use . . . The diameter B of the chamferred portion 23 is set equal to or slightly larger than the diameter A of the inlet 12a of the socket 12.
2. For a light load use . . . The diameter B of the chamferred portion 23 is set slightly smaller than the diameter A of the inlet 12a of the socket 12.

Figure 8:
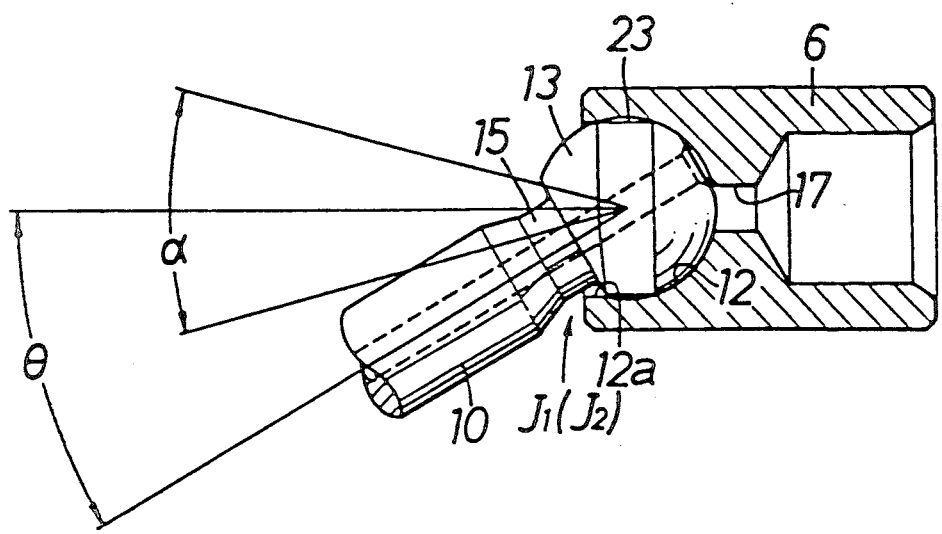
Figure 9:
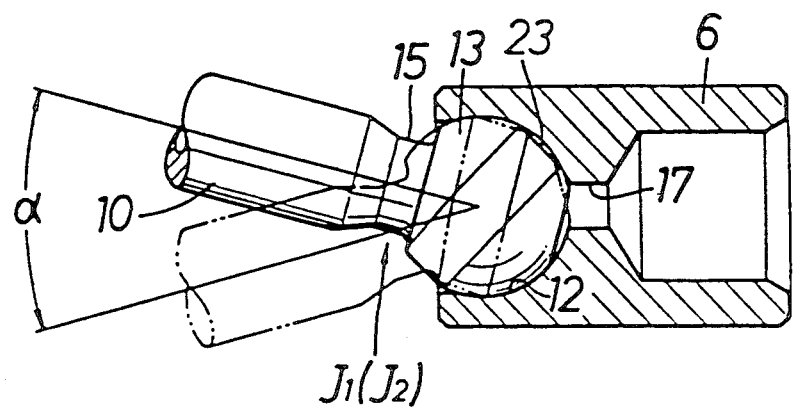

After the socket 12 and the ball 13 have been subjected to surface hardening treatment, the ball 13 can be fitted into the socket 12 by first aligning the axis of the chamferred portion 23 with the center of the inlet 12a of the socket 12 and then press-fitting the chamferred portion 23 into the inlet 12a by means of a press-fitting machine in the afore-mentioned case 1 or by a manual operation in the case 2, as shown in FIG. 8. Though, during this assembling process, the connecting rod 10 is inclined at a large angle $\theta$ with respect to the inlet 12a of the socket 12, the presence of the small diameter neck portion 15 can avoid an interference between the peripheral portion of the inlet 12a of the socket 12 and the connecting rod 10.

In this embodiment, the axes of the chamferred portion 23 of ball 13 and the inlet 12a of socket 12 of each joint $J_1$, $J_2$ do not come into alignment with each other in the normal range of swinging movements of the connecting rod 10, as a result of which each ball joint $J_1$, $J_2$ can have a high strength against disassembly and the ball 13 can be prevented from falling off the mating socket 12 even with a tensile load acting upon the connecting rod 10.

Figure 10:
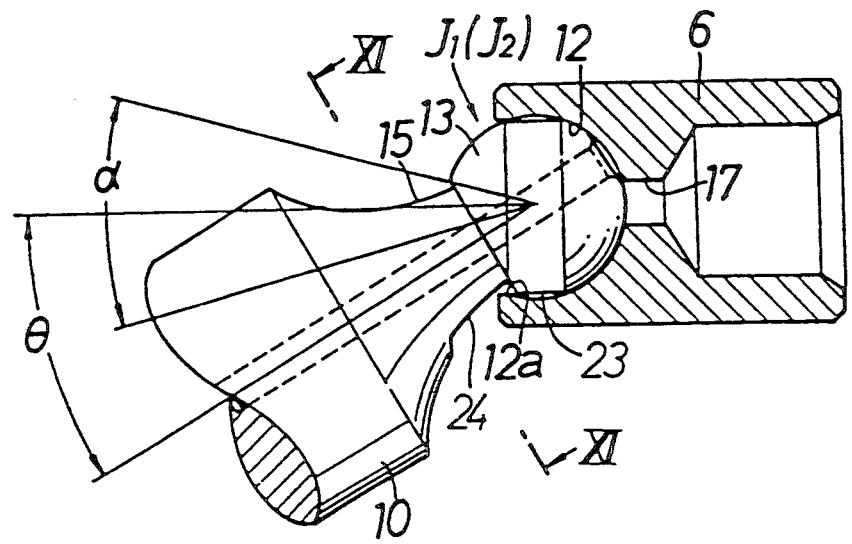
Figure 11:
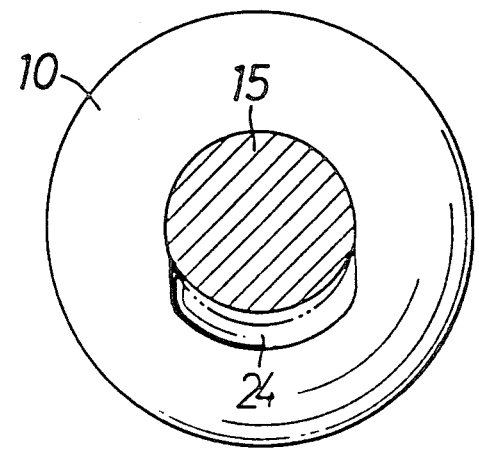
Figure 12:
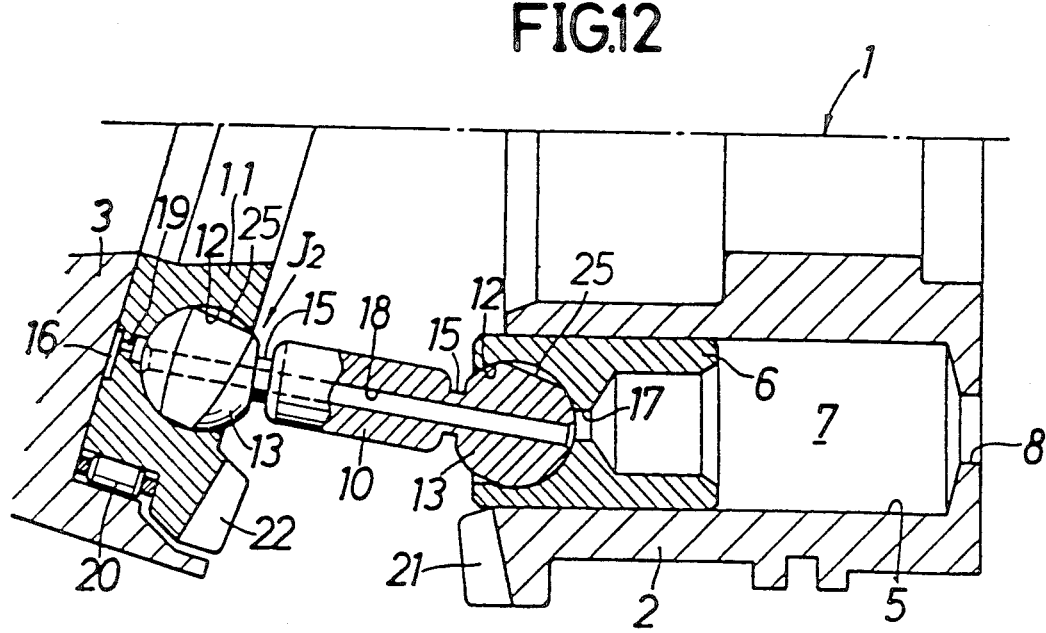

FIGS. 10 and 11 show the third embodiment according to the invention and this embodiment is substantially identical to the second embodiment in structure except that there is further provided a relief 24 in the neck portion 15 of the connecting rod 10 at a location near the chamferred portion 23. In the figures, parts corresponding to those of the second embodiment are denoted by the same reference numerals and characters.

In this third embodiment, even in a case where it is arranged to fit the ball 13 into the socket 12 while inclining the connecting rod 10 at quite a large angle relative to the inlet 12a of the socket 12 in an assembling operation, the relief 24 serves to avoid undesirable interference between the peripheral portion of the socket inlet 12a and the neck portion 15. The arrangement that enables the angle of the connecting rod 10 inclined during assembly to be set larger leads to an advantage that the angle $\alpha$ of normal swinging movements of the connecting rod 10 is permitted to increase correspondingly.

Furthermore, FIGS. 12-15 show the fourth embodiment according to the invention, which is an improvement of the afore-mentioned second embodiment. Therefore, corresponding parts are designated by the same reference numerals and characters and only parts thereof which differ from the second embodiment will be described hereinafter.

Figure 13:
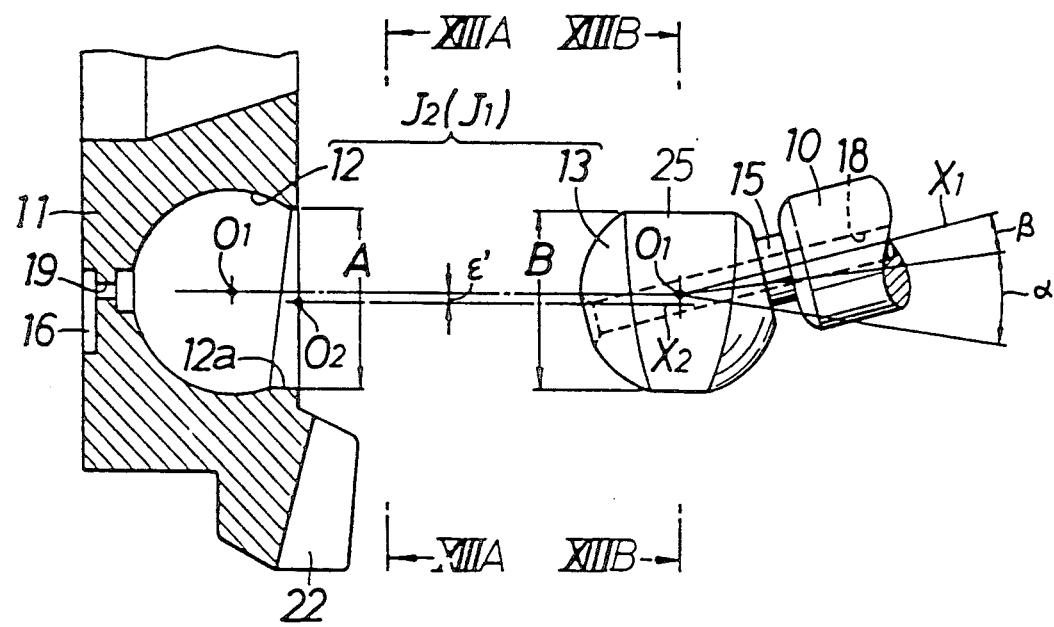
Figure 13A:
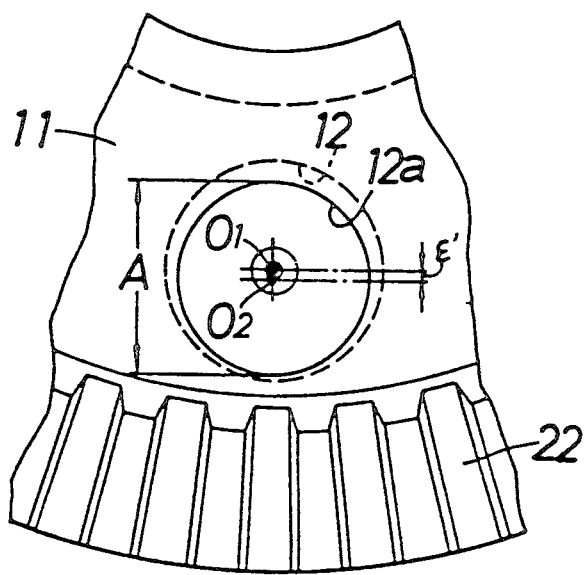
FIG. 13A is a view seen in the direction of an arrow XIIIA—XIIIA in FIG. 13.
Figure 13B:
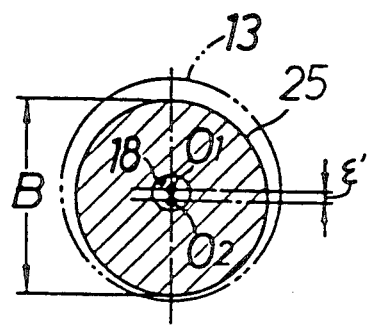
FIG. 13B is a sectional view taken along a line XIIIB—XIIIB of FIG. 13.

In this fourth embodiment, the inlet 12a of the socket 12 is offset a predetermined amount of distance $\epsilon$ from the center $O_1$ of the socket 12 and this offsetting is to such an extent that the periphery of the inlet 12a does not yet inscribe the profile of the socket 12 when viewed in a plan from the inlet 12a side as shown in FIG. 13A.

Moreover, an annular or tubular chamferred portion 25 is formed on each ball 13 and this chamferred portion 25 serves to permit fitting of the ball 13 into the inlet 12a of the socket 12 only when the connecting rod 10 is further inclined a predetermined angle $\beta$ outside the normal swinging range $\alpha$.

In addition, the chamferred portion 25 is formed to have its center offset relative to the center $O_1$ of the ball 13 by the same amount as the offset amount $\epsilon$ of the inlet 12a in a direction opposite to the direction of inclination of the connecting rod 10.

Figure 14:
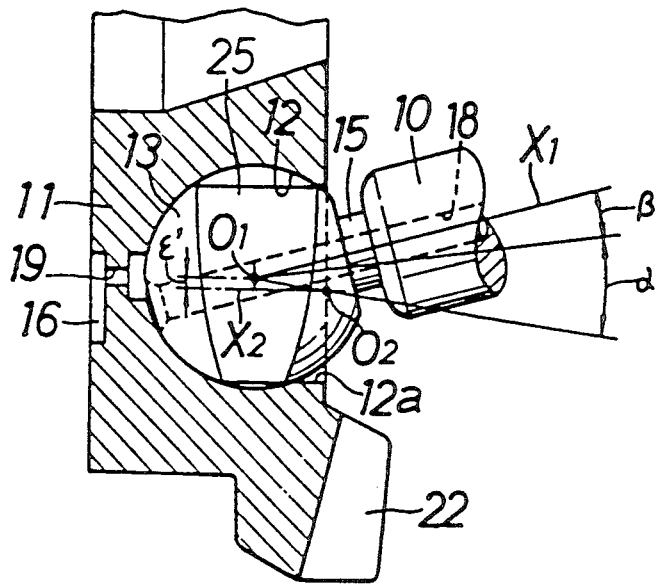

In assembly, after the socket 12 and ball 13 have been subjected to surface hardening treatment, the axis $X_1$ of the connecting rod 10 is brought into alignment with the center $O_1$ of the socket 12 and moreover the axis $X_2$ of the chamferred portion 25 is aligned with the center $O_2$ of the inlet 12a, as shown in FIG. 13. This location enables a following fitting operation of the ball 13 into the socket 12 as shown in FIG. 14.

Figure 15:
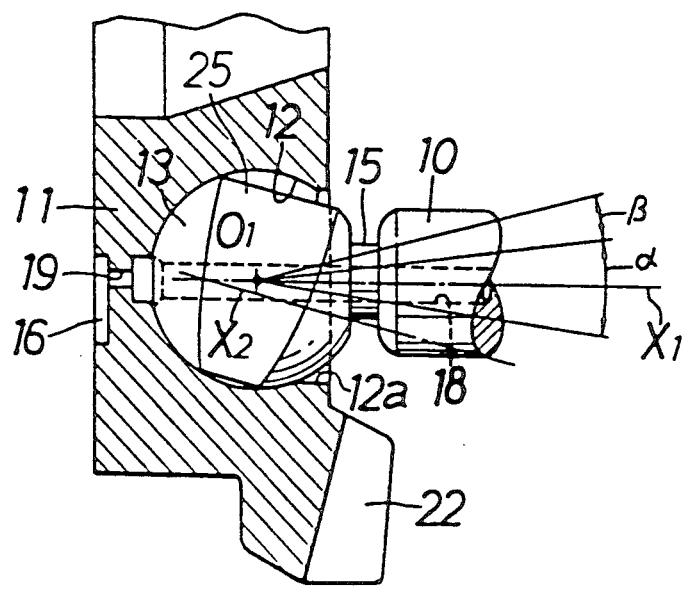

As has been described above, according to this embodiment, since the tubular chamferred portion 25 on the ball 13 is formed so as to be offset a predetermined amount of distance in a predetermined direction from the center of the ball 13, the chamferred portion 25 is to have such a varied width as shown in FIG. 15 and therefore, even with the axis $X_2$ of the chamferred portion 25 being inclined relative to the axis $X_1$ of the connecting rod 10, distances from respective points on the chamferred portion 25 to the opening of the hydraulic fluid port 18 at an end of the ball 13 as measured along the ball surface are made uniform. In other words, the chamferred portion 25 does not have such a point as extremely closer to the port opening than the other points and so fluid leakage from the opening of the port 18 to the chamferred portion 25 can be suppressed to a possible extent and a high hydraulic pressure can be maintained in the hydraulic pocket 16.

Incidentally, this embodiment may also have a relief at the neck portion like the third embodiment.

Throughout all the embodiments described above, the proposed arrangements have been employed in both of the ball joints $J_1$ and $J_2$ provided at the opposite ends of the connecting rod. Such arrangement may, however, be applied only to one of the ball joints.

What is claimed is:

1. A swashplate type hydraulic device comprising a cylinder block having an axis, a plurality of plungers arranged annularly around the axis of the cylinder block and slidably fitted in the cylinder block, a shoe member disposed at an angle to the axis of the cylinder block for synchronous rotation with the block, and connecting rods including at least one of which is connected at opposite ends thereof to the shoe member and associated plunger via ball joints, respectively, at least one of the ball joints comprising a spherical socket having a longitudinal section of major arc formed in one of said shoe member and said plunger and a ball formed at one end of the connecting rod and fitted into the socket for swinging motion of the connecting rod therearound, wherein the socket has an inlet whose center is offset by a predetermined amount of distance from the center of the socket so as to inscribe at a periphery of the inlet the profile of the socket when viewed in a plan from the side of the inlet, and the ball is formed with a cylindrical portion which has a center offset from the center of the ball by an amount equal to said predetermined offset amount of the center of the inlet and which is capable of fitting into the inlet, the centers of the inlet and the cylindrical portion being offset relative to each other in a state of the ball being fitted into the socket.

2. The device according to claim 1, wherein in said state of the ball being fitted into the socket the center of the cylindrical portion of the ball is offset from the center of the socket in a direction opposite to the offset direction of the center of the inlet relative to the center of the socket.

3. The device according to claim 1, wherein said cylindrical portion on the ball has an axis parallel to an axis of the associated connecting rod.

4. The device according to claim 3, wherein the connecting rod has a normally operating position which is offset by an angle of about 180° around the axis of the connecting rod from a position at which the ball is fitted into the socket.

5. A swashplate type hydraulic device comprising a cylinder block having an axis, a plurality of plungers arranged annularly around the axis of the cylinder block and slidably fitted in the cylinder block, a shoe member disposed at an angle to the axis of the cylinder block for synchronous rotation with the block, and connecting rods including at least one of which is connected at opposite ends thereof to the shoe member and associated plunger via ball joints, respectively, at least one of the ball joints comprising a spherical socket having a longitudinal section of major arc formed in one of said shoe member and said plunger and a ball formed at one end of the connecting rod and fitted into the socket for swinging motion of the connecting rod therearound, each the connecting rods being formed with a hydraulic fluid port which extends along the axis of the rod to provide a communication between the cylinder block and the shoe member, wherein the socket has an inlet with a center thereof being offset by a predetermined amount of distance from the center of the socket and the ball is formed with a tubular chamferred portion for permitting fitting of the ball into the inlet of the socket when the connecting rod is inclined a predetermined angle in a predetermined direction to a position outside a range of normal swinging motion thereof, the tubular chamferred portion having a center which is offset relative to the center of the ball by an amount equal to said predetermined offset amount of distance of the inlet in a direction opposite to the inclined direction of the connecting rod.

6. The device according to claim 5, wherein a neck portion of a small diameter is formed at a boundary area between the ball and a rod portion of the connecting rod.

7. The device according to claim 6, wherein the neck portion is formed with a relief at a position thereof near the chamferred portion.

8. The device according to claim 5, wherein said tubular chamferred portion is formed on the ball such that distances from respective points on the chamferred portion to an opening of the hydraulic fluid port made at an end of the ball, which are measured along the surface of the ball, are made uniform.

* * * * *